Figure 1:
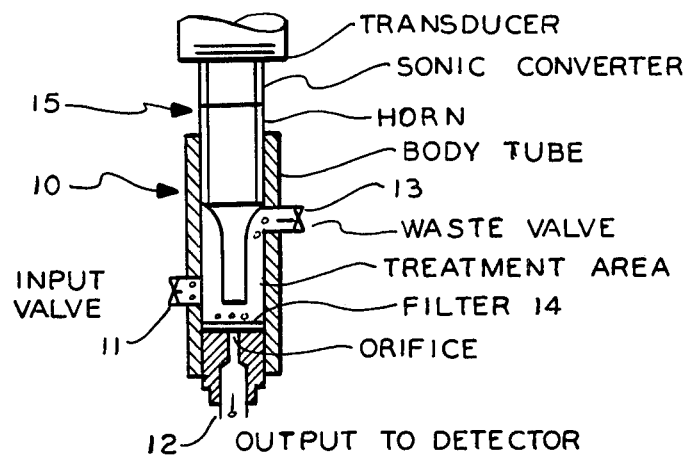

United States Patent [19]

Stoker

[11] Patent Number: 4,615,984
[45] Date of Patent: Oct. 7, 1986

[54] DISSOCIATION OF LIGAND-BINDER COMPLEX USING ULTRASOUND

[75] Inventor: Ronald L. Stoker, Bountiful, Utah

[73] Assignee: Becton Dickinson & Company, Franklin Lakes, N.J.

[21] Appl. No.: 582,949

[22] Filed: Feb. 23, 1984

[51] Int. Cl.[4] .............. G01N 33/543; G01N 33/545; B06B 1/00; C12N 13/00

[52] U.S. Cl. ...................................... 436/518; 134/1; 134/184; 204/157.42; 204/157.62; 422/69; 422/71; 422/128; 435/173; 436/531; 436/536; 436/824

[58] Field of Search ............... 204/157.1 S, 158 S, 204/157.42, 157.62; 436/536, 824, 518, 531; 134/1, 184; 422/20, 128, 69, 71; 435/173; 260/112 R

[56] References Cited

U.S. PATENT DOCUMENTS

| | | | |
|---|---|---|---|
| 3,003,707 | 10/1961 | Lecher | 204/157.1 S |
| 3,492,212 | 1/1970 | Searcy | 435/173 X |
| 3,550,586 | 12/1970 | Balamuth | 435/173 X |
| 3,825,481 | 7/1974 | Supitilov | 422/128 X |
| 4,059,685 | 11/1977 | Johnson | 436/533 |
| 4,180,383 | 12/1979 | Johnson | 422/69 |
| 4,261,828 | 4/1981 | Brunner et al. | 210/287 |
| 4,389,253 | 6/1983 | Nishimura et al. | 134/1 |

FOREIGN PATENT DOCUMENTS

| | | | |
|---|---|---|---|
| 1015962 | 1/1966 | United Kingdom | 134/1 |
| 1303823 | 1/1973 | United Kingdom | 204/157.62 |

Primary Examiner—Esther M. Kepplinger
Assistant Examiner—Patricia Kate White
Attorney, Agent, or Firm—Elliot M. Olstein

[57] ABSTRACT

A ligand is dissociated from a binder specific for the ligand by directing a beam of ultrasound at the complex of ligand and binder. The procedure may be employed in a solid phase assay to separate a labeled form of ligand, employed as a tracer, from a binder supported on a solid support.

14 Claims, 2 Drawing Figures

DISSOCIATION OF LIGAND-BINDER COMPLEX USING ULTRASOUND

This invention relates to the dissociation of a complex of a ligand bound to a binder which is specific for the ligand. More particularly, this invention relates to an assay procedure wherein the ligand is dissociated from a complex of ligand bound to a binder which is specific for the ligand.

In many cases, it is desirable to dissociate a ligand from a complex of a ligand bound to a binder which is specific for the ligand. Thus, for example, in an assay for an analyte wherein the binder used in the assay is to be reused in the assay, it is necessary to dissociate the complex of ligand (labeled and/or unlabeled ligand) which is bound to a binder used in the assay so as to permit reuse of the binder. In general, the binder is regenerated for reuse in the assay by contacting the binder supported on a solid support with a suitable elution liquid, such as aqueous methanol to elute the bound ligand from the binder by dissociation of the ligand-binder complex.

As another example, in some assays, the sample containing analyte is incubated with tracer and binder for both the analyte and tracer to form a bound tracer fraction (tracer bound to binder), and a free tracer fraction. Subsequently, the free tracer fraction is separated from the sample by contacting the sample with a binder for the tracer supported on a solid support. The tracer bound to the supported binder is then dissociated from the binder so that it can be passed to a suitable detector for determining the free tracer fraction. The supported binder may or may not be reused in the assay.

Although it is known in the art that a ligand may be dissociated from its binder in both non-reusable assays, and reusable assays, there is a need for further improvement in such a procedure; e.g., decrease of the time for dissociation of ligand and binder and/or increase in the amount of ligand dissociated.

In accordance with one aspect of the present invention, there is provided an improved process for dissociating a complex of a ligand bound to a specific binder for the ligand wherein a beam of ultrasound is directed at the complex to dissociate and separate the ligand from the binder. The beam of ultrasound may be directed against the complex simultaneously with contacting of the complex with a liquid. The liquid may or may not be an eluting liquid which is known to aid in the dissociation of such complexes.

The beam of ultrasound which is directed at the complex has a frequency of at least 20,000 cycles per second. In general, the frequency of the ultrasonic beam does not exceed about 50,000 cycles per second. The intensity of the ultrasound beam may be varied depending upon whether or not the binder portion of the complex is to be reused. Thus, if rapid separation of ligand from the complex is desired, without the ability to reuse the binder, the intensity of the ultrasound can be increased so as to achieve more rapid dissociation. In the case where the binder is to be reused, then the intensity of the ultrasound is controlled so as to provide for dissociation of the complex without destruction of the binder.

In addition to the control of frequency, if the binder is to be reused, it may be necessary to control the power output so as to prevent an excess build-up of heat. In general, the power output is from 100 to 400 watts. If the solid binder does not have to be reused, then the power wattage may be turned up so dissociation occurs in a faster time period.

The size of the ultrasonic beam may be determined by using the correct converter and booster horn. In order to convert electrical power to mechanical power, a converter or transducer is used. This is typically a quartz or lead zirconate titanate. The waves generated by this transducer are modified by a converter and booster horn to increase the amplitude. To avoid energy losses, the converter is mounted at its nodal plane, where there is a minimum amount of motion. As generally known in the art, the power derived at the end of the horn can then be modified by changing diameter, length, etc. of the horn.

Although applicant does not intend to be limited by any theoretical reasoning, it is believed that the beam of ultrasound functions in one or more of the following ways in accomplishing dissociation of the ligand-binder complex:

1. Compression and decompression of the waves vibrate the complex with enough energy to aid in the dissociation.

2. Micro air bubbles which are present in the binder are compressed at a high velocity which causes oscillation of such air bubbles, resulting in additional waves being propagated in any liquid which is used in combination with the sound waves. In this respect, the micro air bubbles function as a secondary transducer.

3. The movement of micro bubbles in any liquid used results in microstreaming, which results in more movement at the complex as well as providing liquid at the complex liquid interface.

4. A high intensity application of ultrasound results in cavitation, which aids in dissociation of the complex. The cavitation can be controlled by adjusting the frequency, amplitude, and power of the ultrasonic beam.

5. A high intensity application of ultrasound produces heat. This heat could increase the kinetics of dissociation. If the heat was unnecessary or detrimental to the assay, it could be controlled by use of a water-cooled jacket.

The following gives some insight into the principles behind the use of ultrasound; however, the invention is not limited thereby.

In a liquid media, an ultrasonic transducer releases a rapid succession of shock waves. The acoustic energy is transmitted through the liquid media by the back and forth motion of molecules along the direction of wave propagation. This motion produces alternate compressions and rarefactions which in turn create cavitation. Cavitation is the formation of small oscillating cavities throughout the liquid. The collapsing of the cavities produces shock waves which puts additional energy against the ligand and binder. The cavitation puts energy into the system and makes dissociation of bound ligand faster and more efficient.

The present invention is particularly applicable to an assay wherein the complex of ligand and binder is formed as part of the assay procedure. Thus, for example, in such assay procedures, the binder may be an antibody, in which case the ligand which is bound to the antibody may be either an antigen, a hapten, or an antibody which is specifically bound by the antibody which is the binder. For example, if the ligand is an antibody, then the binder may be an antibody produced in response to the antibody which is the ligand. Similarly, the binder may be an antigen or hapten, in which case the ligand is an antibody specific for such antigen or hapten. The binder may be a substance other than an antibody, antigen or hapten, such as, for example, protein A which is known to selectively bind Fc fragments to antibodies, in which case, the ligand may be an antibody. Similarly, the binder may be a naturally occurring substance, in which case, the ligand would be an antigen or hapten which is specifically bound by such naturally occurring substance; for example, the binder could be intrinsic factor and the hapten could be Vitamin $B_{12}$.

The ligand which is bound to the binder, and which is subsequently dissociated from the binder, may be a tracer, in which case the ligand is labeled with a detectable marker. In many cases, the ligand which is bound to the binder is comprised of both labeled ligand (tracer) and unlabeled ligand.

In an assay procedure wherein the ligand is dissociated from a complex of ligand and binder, the binder is generally supported on a solid support, of a type employed in a solid phase assay. Thus, for example, in accordance with one assay procedure, in an assay for a ligand, which, for example, may be an antigen, a sample suspected of containing the ligand (analyte), and an appropriate tracer (the ligand or appropriate analog thereof labeled with a suitable marker) are contacted with a binder; in particular, an antibody supported on a solid suppport, and the ligand and tracer compete for a limited number of binding sites on the supported antibody. The amount of tracer which is bound to the antibody is inversely proportional to the amount of ligand in the sample. After separating the sample from the supported binder, the ligand (tracer and analyte) bound to the antibody on the solid support is removed (dissociated) therefrom by contacting the supported antibody with a liquid, while focusing a beam of ultrasound against the supported binder. Depending on the manner in which the dissociation is accomplished, the binder may be reused in the assay.

In accordance with another type of assay procedure, the ligand to be assayed (analyte) and tracer (the ligand or appropriate analog thereof labeled with a suitable marker) are incubated with a soluble binder for the analyte and tracer and the incubated sample is contacted with a binder for the analyte and tracer supported on a solid support to bind any tracer or analyte which has not been previously bound by the soluble binder. After separating the sample from the supported binder, the complex of ligand (analyte and tracer) bound to the binder on the solid support may be dissociated by contacting the supported binder with a liquid while focusing a beam of ultrasound against the supported binder. Depending on the manner in which the dissociation is accomplished, the binder may be reused in the assay.

In accordance with further procedure, the sample containing a ligand (analyte), which is an antigen having multiple binding sites, is contacted with a tracer in the form of a binder for the analyte which has been labeled with an appropriate marker. As a result of such contact, the sample includes bound tracer (a complex of the labeled binder bound to the antigen) and free tracer (labeled binder which is not bound to the antigen).

The mixture is then contacted with a supported binder, which supported binder is specific for the antigen, whereby the bound tracer (complex of the antigen bound to the labeled binder) may be dissociated from the supported binder by use of a liquid and a beam of ultrasound.

In the hereinabove described various assay procedures, the amount of tracer in the bound and/or free fraction is determined as a measure of ligand in the sample (analyte) by use of a standard curve which is produced by running the assay on samples containing known amounts of analyte.

The supports employed for supporting the supported binder employed in the assay may be any one of a wide variety of supports of the type used in solid phase assays. As known in the art, such supports include suitable polymers, e.g., polystyrene; polypropylene, crosslinked agarose, bacterial cells, ion exchange, resins, cotton as described in U.S. Pat. No. 4,200,625; and supports of the type described in U.S. Pat. No. 4,069,685, etc. Similarly, the binder may be supported on the support by any one of a wide variety of known procedures including adsorption, covalent coupling, etc.

The tracer which is employed in the assay is dependent upon the analyte to be determined in the procedure. The tracer is comprised of a ligand labeled with a suitable detectable marker, such as a radioactive isotope, a fluorescent compound, an enzyme, a chemiluminescent substance, etc. Tracers of the type generally used in an assay are included as a ligand which may be dissociated from a complex of ligand and binder.

In accordance with a preferred procedure, the supported binder used in the assay is in a flowthrough chamber, whereby sample, liquid and other components may be caused to flow over the binder through the chamber.

In accordance with a particularly preferred procedure, the supported binder is reused in the assay and, accordingly, the liquid, as well as the intensity of the ultrasonic beam are selected in a manner such that the ligand is dissociated from the supported binder, without destroying the binding ability of the supported binder. The liquid which is preferably used in an assay in which the binder is to be reused is preferably a liquid which aids in the dissociation of the complex without destroying the binder, often referred to as an eluting liquid or buffer.

As representative examples of suitable eluting liquids for use in dissociating a complex of a ligand bound to a binder, in the case where the binder is to be reused in the assay, there may be mentioned eluting liquids of the type described in U.S. Pat. No. 3,896,217. A particularly preferred eluting liquid is aqueous methanol.

As representative examples of another type of eluting liquid, there may be mentioned a liquid which is at an acidic pH, which is no greater than 3.0 and at which the binding ability of binder is not destroyed; i.e., the eluting liquid is not made too acidic. In general, the eluting liquid is at a pH of no less than 1.5, preferably no less than a 2.0. In particular, such eluting liquid is water buffered to a pH as hereinabove described.

The acidic pH may be obtained by the use of any one of a wide variety of acidic buffers. As representative examples of suitable buffers, there may be mentioned: citrates, acetates, glycinates, glutamates, oxalates, tartrates, phosphates, hydrogen chloride, etc. or mixtures thereof. The selection of a suitable buffer is deemed to be within the scope of those skilled in the art from the teachings herein.

The buffer is employed in a concentration which provides the desired eluting, without destroying the binding ability of the binder. In some cases, the eluting ability is enhanced by increasing the salt concentration (ionic strength) of the solution. Such increases in salt concentration may be effected by increasing the concentration of the buffer or by the addition of a water soluble salt which does not adversely affect the binder. As representative examples of such salts, there may be mentioned: water soluble salts of an alkali metal or ammonium, such as halides; sulfates, nitrates, phosphates, carbonates, bicarbonates, etc.; or water soluble transition metal salts, such as a nitrate, halide, etc. or the like. As hereinabove noted, the total salt concentration, including buffer, is one which provides the desired eluting without destroying the binder, and in general, the salt concentration does not exceed 4M, and in most cases does not exceed 2M. In general, the salt concentration is at least 0.01M, when such salt is employed.

The procedure of the present invention, in the case where the supported binder of the binder/ligand complex is not to be reused, may be easily accomplished by continuous flow cell equipped with an ultrasonic horn (comprised of transducer, sonic converter and horn), as available from Heat System Ultrasonics, Plainview, N.Y.

For example, in such an operation, complex of ligand bound to a binder on a solid support; for example, solid beads, is introduced into the flow cell equipped with suitable valving, lines and, for example, a filter or other means for retaining the complex in the cell. The transducer is turned on to dissociate ligand from supported binder (the ligand may be comprised of analyte and tracer), and the separated ligand is then passed to a suitable detection system for the tracer. The supported binder is then removed from the cell and passed two ways.

The procedure of the present invention may also be easily accomplished in a flowthrough chamber of the type described in U.S. Pat. No. 4,059,685, which is modified to include an ultrasonic horn (comprised of transducer, sonic converter and horn), which is available from Heat System Ultrasonics.

Figure 2:
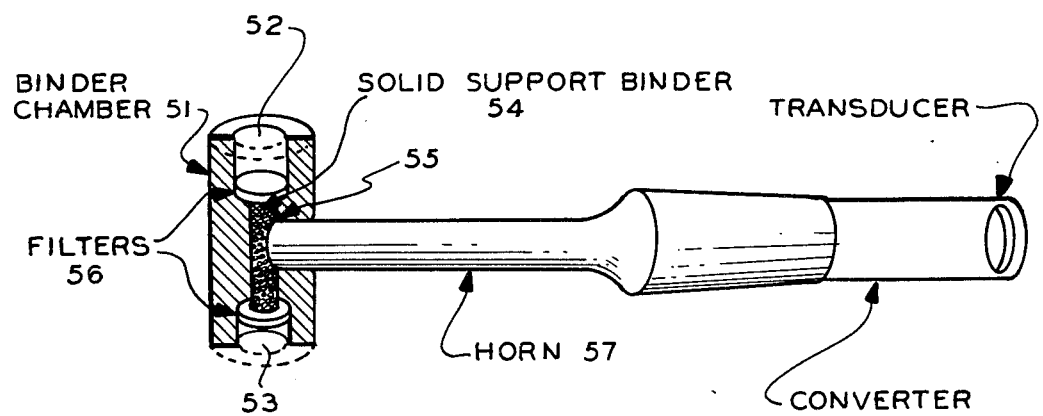

The invention will be further described with respect to embodiments thereof illustrated in the accompanying drawings, wherein:

FIG. 1 is a simplified view of one embodiment of apparatus of the present invention; and FIG. 2 is a simplified view of another embodiment of apparatus of the present invention.

It is to be understood, however, that the scope of the invention is not to be limited to the accompanying drawings.

Referring to FIG. 1 of the drawings, there is shown a flowthrough cell 10, including an inlet port 11, an outlet port 12 for passing tracer to a suitable detector and a second outlet port 13 for passing supported binder to waste after dissociation of the ligand-binder complex. The various ports 11, 12 and 13 are provided with suitable lines and valving so as to enable introduction and withdrawal of the various components.

The flowthrough cell is further provided with means for retaining the supported binder in the flowthrough cell in the form of a filter 14 adjacent to the outlet port 12.

A sonic horn, of a type known in the art, and generally designated as 15 is situated within the interior of the flowthrough cell 10 so that the sonic waves generated by the horn are directed against the ligand-binder complex supported on a solid support, which is retained on the filter 14.

In operation, a complex of ligand-binder supported on a solid support; for example, on appropriate beads, is introduced into the flowthrough cell 10 through line 11, with the supported ligand-binder complex being retained on filter 14.

In accordance with a preferred embodiment, the horn 15 is turned on, while simultaneously introducing a suitable liquid; preferably, an eluting liquid, into the flowthrough cell 10 through line 11, with the eluting liquid, in combination with the sonic horn, dissociating ligand from the binder, with the dissociated ligand in the eluting liquid being withdrawn from the cell 10 through output 12 for passage to a suitable detector. In particular, at least a portion of the ligand in the ligand-binder complex is a tracer so that the dissociated ligand which is passed to the detector may be determined in the detector.

Subsequent to the dissociation, outlet 12 is closed, outlet 13 is opened, and a liquid is introduced into the cell 10 through line 11 for removing the supported binder through outlet 13.

Referring to FIG. 2 of the drawings, there is shown another embodiment, wherein there is shown a flowthrough chamber 51 having an inlet 52 and an outlet 53.

The flowthrough chamber 51 is further provided with a binder supported on a solid support, schematically generally designated as 54, which is retained in a passage 55 connecting the inlet 52 with the outlet 53 by suitable retaining means in the form of filters 56.

The flowthrough chamber 51 is further provided with a sonic horn, generally designated as 57, of a type known in the art, with the horn 57 being situated in a manner such that the sonic waves generated by the horn are directed against the supported binder 54.

In operation, sample containing tracer is passed through chamber 51. In particular, sample containing tracer is introduced through inlet 52 for passage through the supported binder 54 in passage 55, with the sample being withdrawn through outlet 53. The tracer becomes bound to the supported binder 54 to produce a complex of tracer bound to the supported binder.

Subsequently, the sonic horn 57 is turned on, and a suitable eluting liquid is passed over the supported binder 54. The combination of eluting liquid and sonic waves dissociate the tracer from the binder, with the tracer being withdrawn from the chamber 51 through outlet 53. As known in the art, such tracer may be passed to a suitable detector.

In addition, the supported binder may be reused in the assay.

The present invention will be further described with respect to the following examples; however, the scope of the invention is not to be limited thereby:

EXAMPLE 3 ml of phosphate buffered saline, 100 $\mu$l of radioactive labeled digoxin tracer (125 I-digoxin), and 100 $\mu$l of BioRad Immunobeads to which rabbit anti-digoxin antisera was coupled were added to plastic test tubes. The solutions were allowed to incubate for one hour at room temperature. Following the incubation, the solution was centrifuged at 2700 rpm in a Dynac II Centrifuge for 15 minutes. The supernatant was removed and labeled as adsorption. Three milliliters of glycine methanol buffer was added. Some of the tubes were then subjected to ultrasound by putting the end of the transducer horn against the outside of the test tube for 1 minute. (Branson Sonic Power Company, Model W140, 80 watts/cm$^2$, 22 KHZ).

All tubes were then centrifuged for 15 minutes at 2700 rpm. The supernatent was taken off and labeled elution. The precipitate was labeled as such and then all tubes were counted for 1 minute in a Packard Gamma Counter. The following are actual results from this experiment:

|  | Glycine-Methanol Buffer Only | | | | Glycine-Methanol Buffer α Ultrasound | |
|---|---|---|---|---|---|---|
|  | (1) | (2) | (3) | (4) | (1) | (2) |
| Adsorption Solution | 665 | 818 | 649 | 602 | 834 | 667 |
| Precipitate | 31174 | 31483 | 32247 | 31155 | 7046 | 7503 |
| Elution Solution | 4783 | 5470 | 4274 | 5538 | 25743 | 29464 |
| Total | 36622 | 37771 | 37170 | 37295 | 33623 | 37634 |
| % of Total in Elution | 13.1 | 14.5 | 11.5 | 14.8 | 76.6 | 78.3 |
|  | $\bar{x} = 13.5\%$ | | | | $\bar{x} = 77.5\%$ | |

The difference between the mean of 13.5% eluted with glycine-methanol buffer and the mean of 77.5% eluted with glycine-methanol buffer with ultrasound shows the benefits of using ultrasound. Much of the acoustical energy is lost through the test tube wall. The time and intensity of ultrasound application could be lowered if acoustical energy was coupled directly to the solid support.

The present invention is particularly advantageous in that it permits dissociation of ligand from a complex with binder, with the option of reusing the binder. In addition, such dissociation may be accomplished with or without taking precautions to permit reuse of the binder. Furthermore, such dissociation may be easily accomplished independently of the selection of a particular eluting liquid, and in fact, such dissociation may be accomplished with a liquid other than a liquid which is known to be suitable for eluting ligand from a binder.

Furthermore, it is possible to dissociate ligand from such complexes with greater efficiency; i.e., in a shorter period of time and/or with increased removal of ligand from the complex.

Numerous modifications and variations of the present invention are possible in light of the above teachings and, therefore, within the scope of the appended claims, the invention may be practiced otherwise than as particularly described.

What is claimed is:

1. A process for dissociating a complex of a ligand bound to a binder specific for the ligand, comprising:
   directing a beam of ultrasound at a complex of a ligand bound to a binder specific for the ligand for a time and under conditions effective to separate the ligand from the binder.

2. The process of claim 1 wherein the complex is in contact with a liquid at the time of said directing of said beam of ultrasound at the complex.

3. The process of claim 2 wherein the binder is supported on a solid support.

4. The process of claim 3 wherein said liquid is an eluting liquid.

5. The process of claim 4 wherein the binder is supported on a solid support in a flowthrough chamber and the beam of ultrasound is directed against the binder while an eluting liquid flows through the chamber.

6. The process of claim 5 wherein the binder is an antibody.

7. The process of claim 6 wherein at least a portion of the ligand which is bound to the binder is a ligand labeled with a detectable marker.

8. In an assay wherein a tracer comprising a labeled form of a ligand is bound to a binder specific for the ligand on a solid support to form a complex of tracer and binder on the solid support, the improvement comprising:
   directing a beam of ultrasound at a complex of a tracer comprising a labeled form of a ligand bound to a binder specific for the ligand on a solid support for a time and under conditions effective to separate the tracer from the binder of the solid support.

9. The process of claim 8 wherein simultaneously with the directing of said beam of ultrasound at the complex, said complex is in contact with a liquid.

10. The process of claim 9 wherein said beam of ultrasound has a frequency of at least 20,000 cycles per second.

11. The process of claim 10 wherein said binder is supported on a solid support in a flowthrough chamber and the beam of ultrasound is directed against the binder while a liquid flows through the chamber.

12. The process of claim 11 wherein said liquid is an eluting liquid and the intensity of the beam of ultrasound is controlled to prevent destruction of the binder whereby the binder may be reused in the assay.

13. The process of claim 12 wherein the binder is an antibody.

14. An apparatus, comprising:
   flowthrough chamber; a binder, for specifically binding a ligand, supported on a solid support in said chamber; and ultrasonic means connected to said chamber for producing and directing a beam of ultrasound against said binder.

* * * * *